(12) United States Patent  (10) Patent No.: US 7,945,454 B2
Firozvi  (45) Date of Patent: May 17, 2011

(54) MEDICAL PERSONAL DISPLAY ASSISTANT GUIDE

(76) Inventor: Kashif A. Firozvi, Rockville, MD (US)

(*) Notice: Subject to any disclaimer, the term of this patent is extended or adjusted under 35 U.S.C. 154(b) by 858 days.

(21) Appl. No.: 11/846,745

(22) Filed: Aug. 29, 2007

(65) Prior Publication Data

US 2009/0063190 A1  Mar. 5, 2009

(51) Int. Cl.
*G06Q 10/00* (2006.01)
*G06Q 50/00* (2006.01)
(52) U.S. Cl. ............................................................. 705/2
(58) Field of Classification Search .................. 705/2, 3;
364/401; 707/5; 715/777
See application file for complete search history.

(56) References Cited

U.S. PATENT DOCUMENTS

| | | | |
|---|---|---|---|
| 5,737,539 A * | 4/1998 | Edelson et al. | 705/2 |
| 5,918,208 A * | 6/1999 | Javitt | 705/2 |
| 6,000,828 A * | 12/1999 | Leet | 705/2 |
| 6,317,719 B1 * | 11/2001 | Schrier et al. | 705/2 |
| 6,801,227 B2 * | 10/2004 | Bocionek et al. | 715/777 |
| 2002/0169771 A1 * | 11/2002 | Melmon et al. | 707/5 |
| 2005/0283383 A1 * | 12/2005 | Zammit | 705/2 |
| 2007/0005397 A1 * | 1/2007 | Lee | 705/3 |

* cited by examiner

*Primary Examiner* — Gerald J. O'Connor
*Assistant Examiner* — John A Pauls
(74) *Attorney, Agent, or Firm* — Rahman LLC

(57) ABSTRACT

A system and method of managing medical-related data includes at least one database comprising medical-related data, wherein the at least one database comprises a first module that stores and retrieves data relating to pharmaceutical drugs; a second module that stores and retrieves data relating to medical treatment protocols; a third module that stores and retrieves data relating to healthcare reimbursement data; a fourth module that stores and retrieves data relating to medical billing coding data; and a fifth module that stores and retrieves data relating to medical education data. Furthermore, at least one client system is operatively connected to the at least one database through a communications channel, wherein each of the at least one client system accesses all modules of the at least one database; consolidates data based on user instructions; and broadcasts the consolidated data.

17 Claims, 7 Drawing Sheets

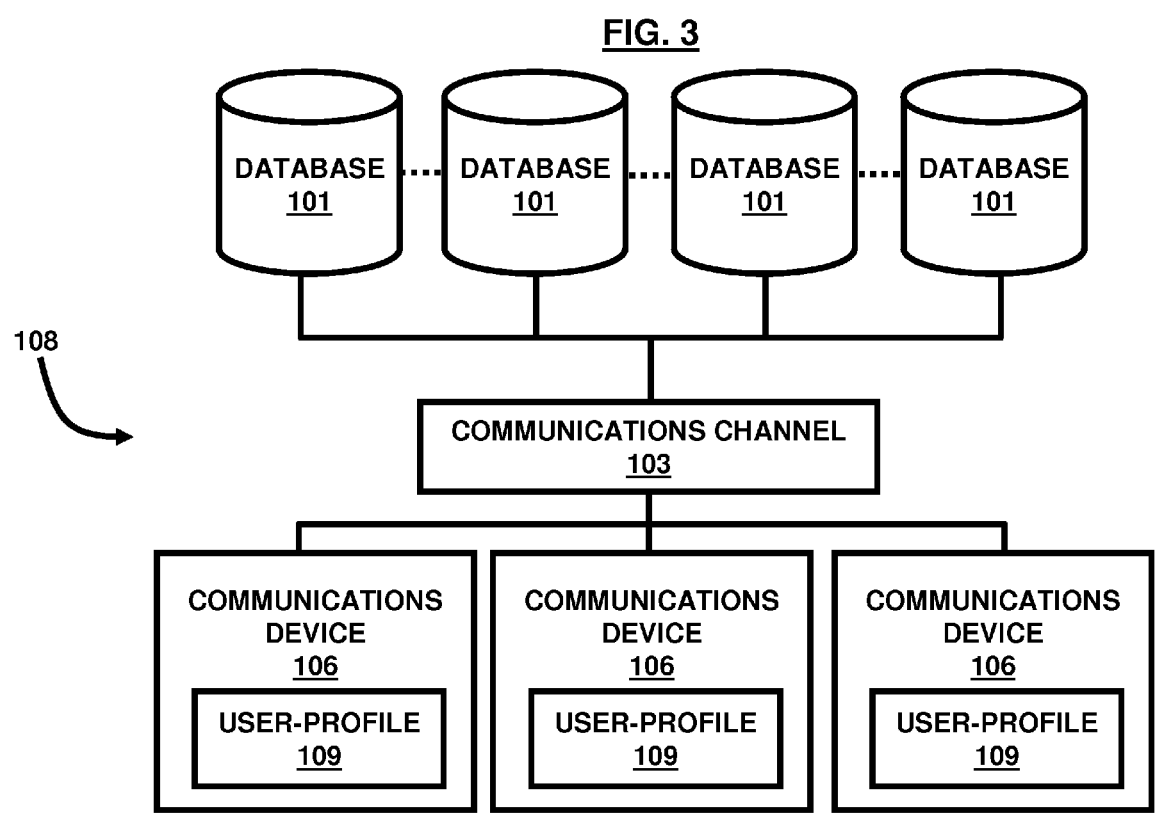

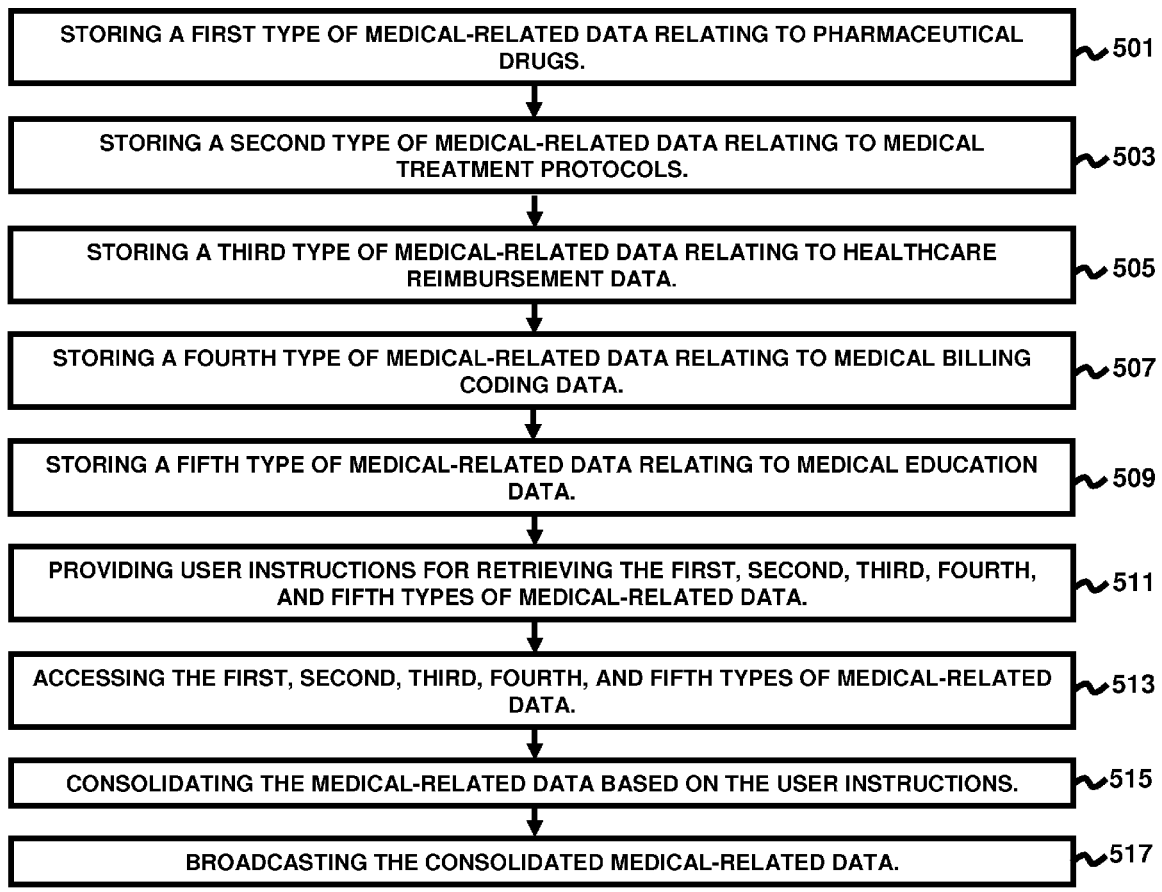

MEDICAL PERSONAL DISPLAY ASSISTANT GUIDE

BACKGROUND

1. Technical Field

The embodiments herein generally relate to medical database systems, and, more particularly, to interactive systems and methods for storing and retrieving medical-related information for health practitioners.

2. Description of the Related Art

Techniques affecting the manner in which medical treatment is delivered to patients is constantly changing based, in part, on rapid advances in technology. For example, medical practitioners have identified the field of oncology to be changing at such a rapid pace in terms of medical and technological advances, thereby making it exceedingly difficult to sufficiently keep an oncology-based practice up do date. Another factor affecting medical practices is government scrutiny as promulgated by increased legislation and regulations. For example, the United States Congress is demanding strict adherence to nationally accepted guidelines to establish a more unified healthcare system. Furthermore, the issues of financing a medical practice that delivers chemotherapy are an ever-dynamic target that requires constant awareness of the different reimbursement protocols for the multitude of healthcare payment plans (i.e., Medicare, private insurance plans, etc.). Clearly, a technique that consolidates the relevant data necessary for a medical practitioner to deliver state-of-the-art quality medical advice and treatment in an efficient and cost-effective manner would provide an improvement to the overall delivery of medical services and the quality of care rendered by medical practitioners. Furthermore, such a technique that utilizes the current advances in information technology to foster medical data consolidation and information retrieval would undoubtedly be beneficial to allow easier use of such a technique by a medical practitioner.

SUMMARY

In view of the foregoing, an embodiment herein provides a database system comprising at least one database comprising medical-related data, wherein the at least one database comprises a first module adapted to store and retrieve data relating to pharmaceutical drugs; a second module adapted to store and retrieve data relating to medical treatment protocols; a third module adapted to store and retrieve data relating to healthcare reimbursement data; a fourth module adapted to store and retrieve data relating to medical billing coding data; and a fifth module adapted to store and retrieve data relating to medical education data. The database system further includes a communications channel operatively connected to the at least one database; and at least one client system operatively connected to the at least one database through the communications channel, wherein each of the at least one client system is adapted to access all modules of the at least one database; consolidate data based on user instructions; and broadcast the consolidated data.

The database system may further comprise a host server operatively connected to the at least one database, wherein the host server is adapted to transmit the medical-related data from the at least one database to the each of the at least one client system through the communications channel. Moreover, each of the at least one client system may comprise a handheld communications device, wherein the handheld communications device may comprise any of a personal display assistant (PDA) and a cellular phone. Additionally, each of the at least one client system may comprise a customizable user-profile, wherein the user-profile is adapted to filter the medical-related data retrievable from the at least one database and transmit medical history data.

Preferably, the first module adapted to store and retrieve data relating to pharmaceutical drugs comprises a first set of computer-executable commands relating to dosing of pharmaceutical drugs; a second set of computer-executable commands relating to an efficacy and effects of the pharmaceutical drugs; a third set of computer-executable commands relating to a cost of the pharmaceutical drugs; a fourth set of computer-executable commands relating to an accessibility and delivery of the pharmaceutical drugs; and a fifth set of computer-executable commands relating to mixing of a plurality of different pharmaceutical drugs and administering the plurality of different pharmaceutical drugs to a patient.

Furthermore, the second module adapted to store and retrieve data relating to medical treatment protocols preferably comprises a first set of computer-executable commands relating to patient data; a second set of computer-executable commands relating to medical decision-making data in accordance with medical industry standards; and a third set of computer-executable commands comprising linking information to the first module relating to pharmaceutical drugs. Preferably, the patient data comprises any of age, illness type, and stage of illness data.

Additionally, the third module adapted to store and retrieve data relating to healthcare reimbursement data preferably comprises a first set of computer-executable commands relating to a cost of a particular medical protocol according to a particular type of medical insurance; a second set of computer-executable commands relating to a determination of whether a particular type of medical treatment is Federal Drug Administration (FDA) approved; and a third set of computer-executable commands relating to patient co-pay data. Preferably, the fourth module adapted to store and retrieve data relating to medical billing coding data comprises a first set of computer-executable commands relating to office visit scenarios for which a medical practitioner may bill a patient; and a second set of computer-executable commands adapted to provide instructions to billing software for linking to a medical insurance supplier for providing healthcare reimbursement for the medical practitioner.

Moreover, the fifth module adapted to store and retrieve data relating to medical education data preferably comprises a first set of computer-executable commands relating to medical literature retrieval; and a second set of computer-executable commands relating to continuing medical education (CME) data. Preferably, the consolidated data is broadcast in any of a text, graphics, audio, and video format. In one embodiment, the medical-related data may comprise oncology-related data. Also, each of the at least one client system is preferably adapted to display a webpage of a medical practitioner office, wherein the webpage comprises a software module adapted to process patient appointments and interoffice communication.

The database system may further comprise a separate database for each one of the modules. Furthermore, each of the at least one client system may comprise an interface adapted to receive the user instructions, wherein the interface preferably comprises any of a microphone, stylus, mouse, and keypad. Preferably, the user instructions comprise any of a user query and a customizable user-profile adapted to instruct the at least one database to transmit particular medical-related data specific to the user instructions.

Another embodiment provides a computer-automated method of managing medical-related data and a program storage device readable by computer comprising a program of instructions executable by the computer to perform the computer-automated method of managing medical-related data, wherein the computer-automated method comprises storing a first type of medical-related data relating to pharmaceutical drugs; storing a second type of medical-related data relating to medical treatment protocols; storing a third type of medical-related data relating to healthcare reimbursement data; storing a fourth type of medical-related data relating to medical billing coding data; storing a fifth type of medical-related data relating to medical education data; providing user instructions for retrieving the first, second, third, fourth, and fifth types of medical-related data; accessing the first, second, third, fourth, and fifth types of medical-related data; consolidating the medical-related data based on the user instructions; and broadcasting the consolidated medical-related data.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 3 illustrates a schematic diagram of a database system according to an alternate embodiment herein;

FIG. 5 is a flow diagram illustrating a preferred method according to the embodiments herein.

DETAILED DESCRIPTION OF PREFERRED EMBODIMENTS

Figure 1:
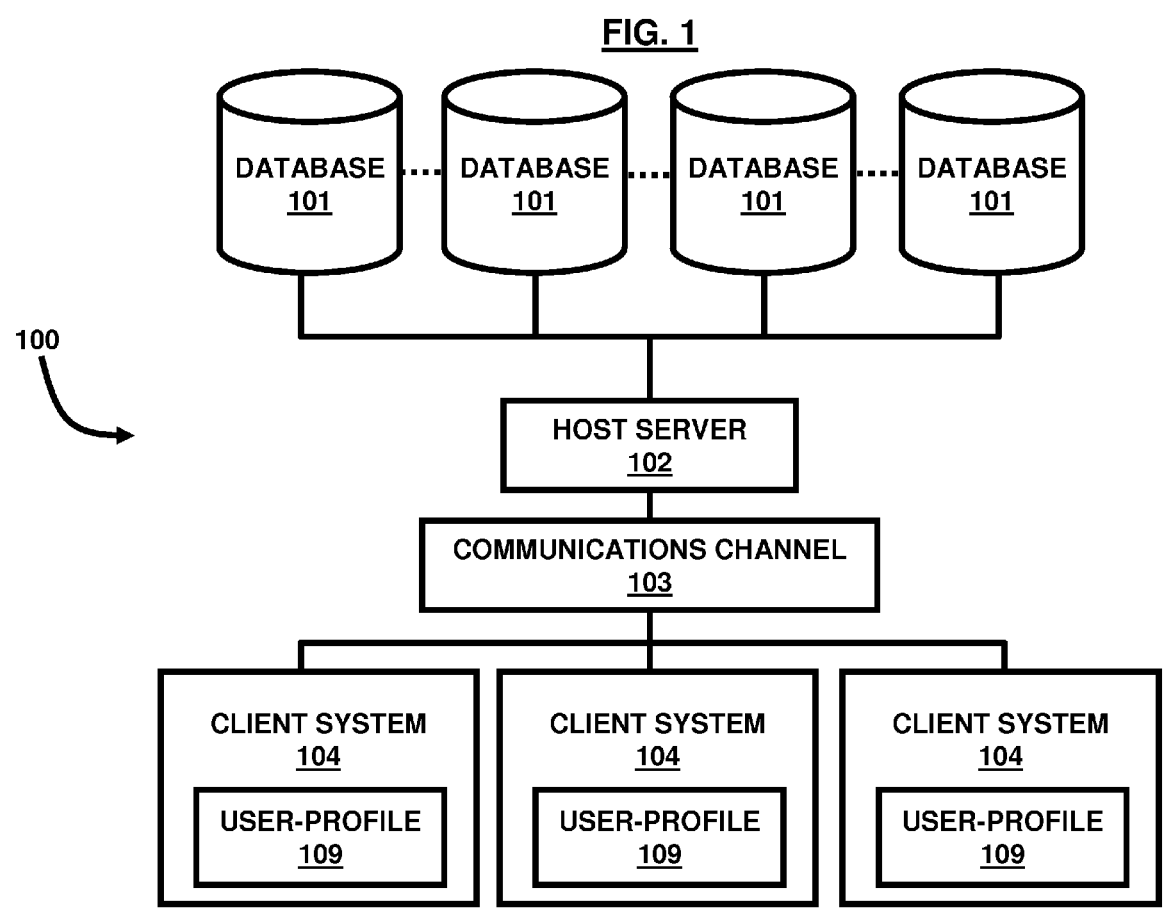
FIG. 1 illustrates a schematic diagram of a database system according to the embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

As mentioned, there remains a need for a technique that consolidates the relevant data necessary for a medical practitioner to deliver state-of-the-art quality medical advice and treatment in an efficient and cost-effective manner in order to provide an improvement to the overall delivery of medical services and the quality of care rendered by medical practitioners. Furthermore, there remains a need for a technique that utilizes the current advances in information technology to foster medical data consolidation and information retrieval to allow easier use of such a technique by a medical practitioner. The embodiments herein achieve this by providing a communications device such as a PDA based system and method to provide information for medical practitioners on the many issues related to the healthcare of patients. While the examples provided herewith are related to oncology, those skilled in the art would readily recognize that the embodiments herein are applicable to other medical subspecialties, and accordingly, the embodiments herein are not restricted to any particular medical subspecialty. Referring now to the drawings, and more particularly to FIGS. 1 through 6, where similar reference characters denote corresponding features consistently throughout the figures, there are shown preferred embodiments.

FIG. 1 illustrates a database system 100 according to an embodiment herein. The database system 100 may be embodied in a host-client environment comprising a plurality of databases 101 that are preferably configured to be interoperable and inter-accessible. The databases 101 are each repositories for various medical-related data and may be maintained, updated, and managed by different entities or by a single entity. A host server 102 is operatively connected to each of the databases 101 and, through a communications channel 103, the host server communicates to at least one client system 104. The communications may be wireless and could be internet-based. In the context of the embodiments herein, the client system 104 is accessible to the medical practitioners (i.e., physicians, nurses, and others providing the medical diagnosis and patient treatment). Furthermore, several client systems 104 may be linked together to serve the needs of a multi-practitioner environment (i.e., several physicians in the same office or several offices in the same medical center, etc.) In one embodiment, the client system 104 is adapted to link to (and/or display) the client's (i.e., physician's office, etc.) office webpage and may include a software-embodied module (not shown) associated with office-related tasks such as patient appointments and interoffice communication (i.e., e-mail communications, text messaging, etc.).

Figure 2A:
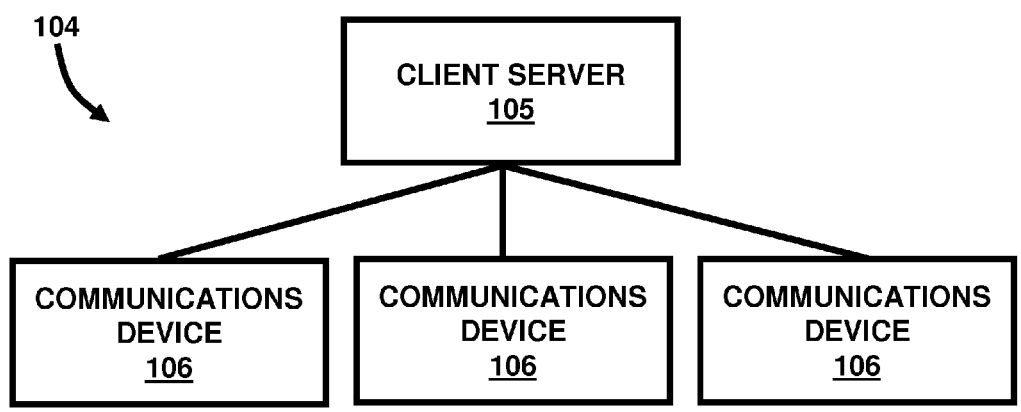
FIGS. 2(A) and 2(B) illustrate schematic diagrams of alternative client systems according to the embodiments herein.

FIG. 2(A) illustrates a first embodiment of the client system 104 of FIG. 1. In this embodiment, the client system 104 includes a client server 105 having linked communication devices 106 preferably embodied as PDAs having an audio speaker and video display component. PDAs are preferred within the context of the embodiments herein due to their user-friendly interactive features (such as graphic user interfaces (GUIs), drop-down menus, voice command, etc.) compact size, and ease of transport. Furthermore, the multi-functionality inherent in many of the current state-of-the-art PDAs allows for a breadth of use (i.e., data storage/retrieval, e-mail capability, text/voice messaging, graphics retrieval/transmission, etc.).

Figure 2B:

FIG. 2(B) illustrates a second embodiment of the client system 104 (of FIG. 1), whereby the client system 104 includes at least one communication device 106 such that a client server 105 (of FIG. 2(A)) is not required, but rather the communication devices 106 are configured to operatively interact directly with the host server 102 via the communications channel 103 (of FIG. 1). Furthermore, the communications devices 106 may be linked to one another or may be independent devices.

FIG. 3 illustrates an alternative database system 108 in accordance with the embodiments herein, which includes a plurality of databases 101 that are accessible to at least one communications device 106 via a communications channel 103. Here, the databases 101 may physically reside at the physician's office, hospital, or research center to allow direct access to and maintenance of the databases 101. Furthermore, those skilled in the art would readily recognize that other types of database systems may be used in accordance with the embodiments herein, and the embodiments herein are not restricted to one particular type of database system environment.

Figure 4A:
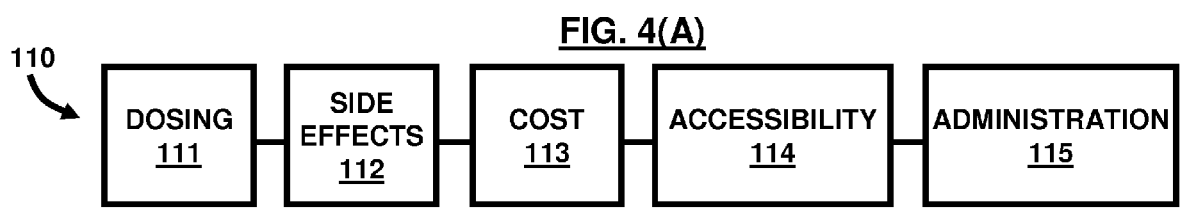
FIGS. 4(A) through 4(E) are block diagrams illustrating several data modules according to the embodiments herein.

As mentioned, the databases 101 (of FIGS. 1 and 3) are each repositories for various medical-related data. FIG. 4(A) illustrates a first module 110 related to pharmaceutical drug data. The first module 110 is preferably configured as computer-executable commands adapted to retrieve data stored in the databases 101 (of FIGS. 1 and 3) related to pharmaceutical drug data. For example, the first module 110 may include a first set of computer-executable commands 111 related to the dosing of pharmaceutical drugs according to the protocols (i.e., the medical guidelines) with reference to the article. For example, a particular drug (for example, Taxol® anti-cancer pharmaceutical drug, available from Bristol-Myers Squibb Company, New York, USA) may be used in three different cancer types, and in each cancer type, Taxol® anti-cancer pharmaceutical drug may be dosed and delivered in different fashions. Therefore, if a physician selects Taxol® anti-cancer pharmaceutical drug, then the first module 110 will present a choice of either breast, lung, or ovarian and then from there, if the physician selects ovarian, the first module 110 presents a list of the exact protocol (regimen) and supplies the article journal and citation) from where the protocol came. A second set of computer-executable commands 112 relates to the efficacy including the side effects of various pharmaceutical drugs. Here, the second set of computer-executable commands 112 generates a list of all the various side effects of various drugs, especially chemotherapies. A third set of computer-executable commands 113 relates to the cost of various pharmaceutical drugs. Here, the third set of computer-executable commands 113 generates a list of the amount that would be reimbursed to a medical practitioner based on the patient's health insurance company. For example, the cost for Drug X is set. However, what the medical practitioner will receive after delivering Drug X to a patient is dependent on the patient's health insurance; Medicare pays a certain price, while other private medical insurers pay other prices. A fourth set of computer-executable commands 114 relates to pharmaceutical delivery and accessibility information including the names and contact information of a particular pharmaceutical drug manufacturer and may include the associated pharmaceutical drug representative located in the area where the medical practitioner is based. A fifth set of computer-executable commands 115 relates to specific information regarding the mixing of various pharmaceutical drugs (and their effects) and administration of the various pharmaceutical drugs in accordance with one another.

Figure 4B:
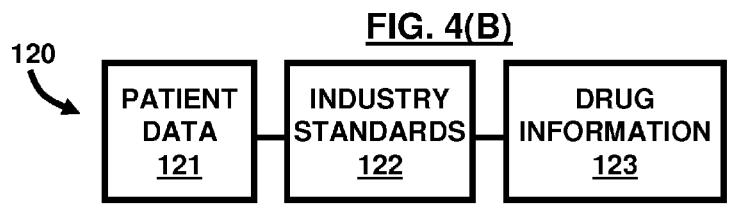

FIG. 4(B) illustrates a second module 120 related to medical treatment protocol data. The second module 120 is preferably configured as computer-executable commands adapted to retrieve data stored in the databases 101 (of FIGS. 1 and 3) related to medical treatment protocol data. For example, the second module 120 may include a first set of computer-executable commands 121 related to the patient data (i.e., age, illness type, stage of illness, etc.). A second set of computer-executable commands 122 relates to the medical decision-making according to industry standards. For example, national guidelines such as those promulgated by the National Comprehensive Cancer Network (NCCN) and American Society of Clinical Oncology (ASCO) are often utilized by oncologists in determining a cancer treatment protocol for a particular patient. As another example, Adjuvant! Online (available from Adjuvant! Inc.) is a web-based tool that oncologists utilize to determine the risk of a relapse and the benefit of chemotherapy. A third set of computer-executable commands 123 provides a data-retrieval link to the first module 110 (of FIG. 4(A)) relating to pharmaceutical drug information, which provides a link from the treatment protocol generated by the second set of computer-executable commands 122 (of FIG. 4(B)) to the type of drug to be used for the particular type of treatment generated by the first module 110 (of FIG. 4(A)). Again with reference to FIG. 4(B).

Figure 4C:
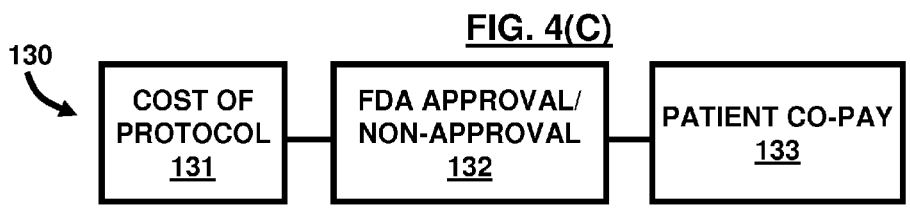

FIG. 4(C) illustrates a third module 130 related to healthcare reimbursement data. The third module 130 is preferably configured as computer-executable commands adapted to retrieve data stored in the databases 101 (of FIGS. 1 and 3) related to healthcare reimbursement data. For example, the third module 130 may include a first set of computer-executable commands 131 related to the cost of a particular medical protocol according to the specific insurance type. For example, a medical practitioner enters "40 year old female with invasive ductal carcinoma, stage III" in the communication device 106 (of FIGS. 2(A) and 2(B)). The third module 130 then provides the medical practitioner with a list of possible regimens that could be used according to national standard guidelines. The pharmaceutical drugs of each regimen, if selected individually then links to the specific drug information. Lastly, once the medical practitioner selects the regimen of interest, the third module 130 allows the medical practitioner to enter what insurance company the patient has and then when the medical practitioner selects Medicare, for example, the third module 130 indicates how much the medical practitioner stands to profit or lose with the particular regimen.

A second set of computer-executable commands 132 relates to whether a particular type of medical treatment has received FDA approval or non-approval. For example, for non-approved FDA treatments a compendia listing may be applicable to a particular treatment, which is a measure that typically indicates to medical practitioners and third party payees of medical services (i.e., insurance companies) that the particular treatment, while not FDA approved, is a medically acceptable and perhaps effective treatment for a particular illness. A third set of computer-executable commands 133 relates to patient co-pay data, which may be different for different patients depending on the insurance type, plan, classification of medical practitioner and treatment, and illness type. For example, in the context of oncology, patients on oral chemotherapies have different co-pays than patients on other types of treatments. This may aid the medical practitioner in the following scenario. A physician orders a particular drug for a patient. The patient returns for a visit with the physician the following week not having taken the drug because the patient discovered that their out-of-pocket expense far exceeded their insurance co-pay for purchasing the drug. Had the physician known that information prior to this, he/she could have planned accordingly or at least informed the patient of this likelihood beforehand.

Figure 4D:
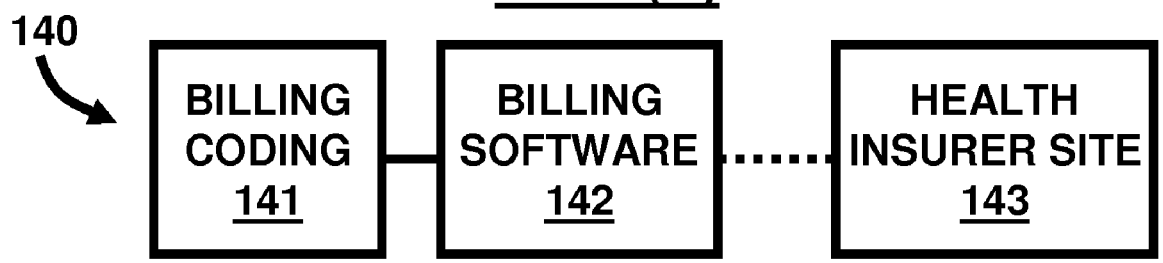

FIG. 4(D) illustrates a fourth module 140 related to medical billing coding data. The fourth module 140 is preferably configured as computer-executable commands adapted to retrieve data stored in the databases 101 (of FIGS. 1 and 3) related to medical billing coding data. For example, the fourth module 140 may include a first set of computer-executable commands 141 related to the various office visit scenarios for which a medical practitioner may bill a patient. For example, the first set of computer-executable commands 141 may include a checklist that describes the type of office visit (i.e., initial examination, follow-up care, office consultation, pharmaceutical drug dispensing, medical treatment, invasive procedure, etc.) and whether and to what extent such an office visit may be billed, if at all. A second set of computer-executable commands 142 may relate to providing instructions to billing software that may be operatively linked to a health insurer site 143 to provide proper billing of the services with respect to health insurance reimbursement.

Figure 4E:
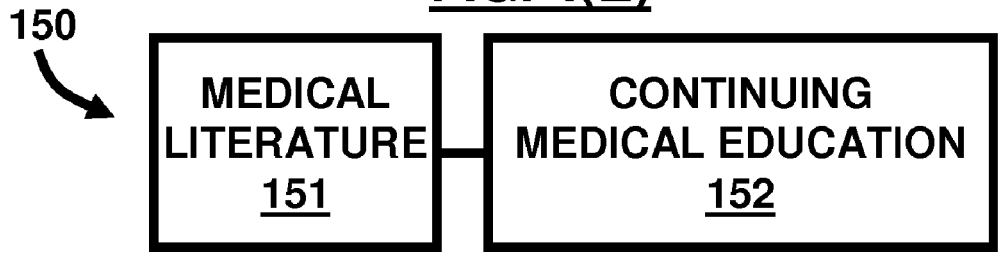

FIG. 4(E) illustrates a fifth module 150 related to medical education data. The fifth module 150 is preferably configured as computer-executable commands adapted to retrieve data stored in the databases 101 (of FIGS. 1 and 3) related to medical education data. For example, the fifth module 150 may include a first set of computer-executable commands 151 that provide a link to medical literature (i.e., textbooks, online databases, journals, articles, graphics, interactive audio/video, etc.). For example, an oncologist might prefer to retrieve abstracts from the Journal of Clinical Oncology or the New England Journal of Medicine. A second set of computer-executable commands 152 may relate to CME data (i.e., literature, courses, lectures, conferences, etc.) that may be relevant to a particular medical practitioner or illness.

Another aspect of the embodiments herein involves targeted distribution of medical information from the databases 101 (of FIGS. 1 and 3) to medical providers. The medical information may be distributed as text, graphics, audio, and/or video to a medical provider via a handheld communications device 106 (of FIGS. 2(A) through 3) and may be a cellular phone or PDA or other type of handheld communications device. The transmission may occur using any type of conventional standard such as digital audio broadcasting (DAB), digital multimedia broadcasting (DMB) (satellite or terrestrial), digital radio mondiale (DRM), digital video broadcasting over handheld (DVB-H), digital video broadcasting—terrestrial (DVB-T), integrated services digital broadcasting (ISDB), MediaFLO™ (available from Qualcomm, Inc.), and other well-known standards.

According to the embodiments herein, a medical practitioner may customize his/her database system 100, 108 (of FIGS. 1 and 3) by establishing a user-profile 109 in the client system 104 or communication device 106 directly. Additionally, the user-profile 109 may serve as a patient tracker system whereby the patient's medical history as well as health insurance type/provisions are continuously updated either directly to the user-profile 109 (on the client system 104 (of FIG. 1) or on the communications device 106 (of FIG. 3)). In this embodiment, after a patient has been evaluated by a medical practitioner either at an office visit or at the hospital, the medical practitioner (or his/her support staff) can enter the data into the user-profile 109 and determine the classification of the visit. This data can then be linked to billing software 142 of the fourth module 140 (of FIG. 4(D)) such that an accurate assessment of the patient's visit can be accurately billed with respect to health insurance reimbursement.

Furthermore, such a user-profile 109 may include specific information pertaining to a particular medical subspecialty, and accordingly may differ from user-to-user. For example, an oncologist may choose to retrieve data from databases 101 (of FIGS. 1 and 3) that are specifically related to oncology. In other words, the user-profile 109 may be configured such that a particular medical practitioner (for example, an oncologist) may choose to only receive data (either on demand or automatically) relevant specifically to his/her medical practice (for example, only relating to oncology). As such an example, an oncologist may desire to be kept apprised of CME conferences relating specifically to subject matter pertaining only to oncology. As such, the user-profile may include instructions for the second set of computer-executable commands 152 of the fifth module 150 (of FIG. 4(E)) to identify only those CME course/conference listings pertaining to oncology thereby serving as a filter for extraneous and non-relevant data being transmitted to the medical practitioner. This filtering process aids in reducing computational loads imposed on the database system 100, 108 (of FIGS. 1 and 3) and improving the user's experience by filtering undesired or non-relevant data.

Operationally, a user may enter a user query via an interface (not shown) (i.e., microphone (for voice command), stylus, mouse, keypad (for text entry), etc.) of the communications device 106 (of FIGS. 2(A) through 3), and relevant data from databases 101 (of FIGS. 1 and 3) are accessed and transmitted back to the communications device 106. The transmitted data may include audio, video, and/or graphics data. Furthermore, the user-profile 109 (of FIGS. 1 and 3) may be adapted to automatically generate relevant data from the databases 101 (of FIGS. 1 and 3) without an actual user query such that the user-profile 109 may include instructions for automatic display/broadcast on the communications device 106 (of FIGS. 2(A) through 3) of the relevant data that matches a particular user's interests as determined by the user-profile 109 (of FIGS. 1 and 3).

FIG. 5 illustrates a flow diagram of a computer-automated method of managing medical-related data according to an embodiment herein, wherein the computer-automated method comprises storing (501) a first type of medical-related data (110) relating to pharmaceutical drugs; storing (503) a second type of medical-related data (120) relating to medical treatment protocols; storing (505) a third type of medical-related data (130) relating to healthcare reimbursement data; storing (507) a fourth type of medical-related data (140) relating to medical billing coding data; storing (509) a fifth type of medical-related data (150) relating to medical education data; providing (511) user instructions for retrieving the first, second, third, fourth, and fifth types of medical-related data (110-150); accessing (513) the first, second, third, fourth, and fifth types of medical-related data (110-150); consolidating (515) the medical-related data (110-150) based on the user instructions; and broadcasting (517) the consolidated medical-related data (110-150).

The embodiments herein can take the form of an entirely hardware embodiment, an entirely software embodiment or an embodiment including both hardware and software elements. The embodiments that are implemented in software include, but are not limited to, firmware, resident software, microcode, etc. Moreover, the embodiments herein may be configured in a stand-alone system designed specifically to the healthcare industry or may be configured in a communications package designed for more generalized use, and which may be implemented by mobile phone manufacturers, for example.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 6:
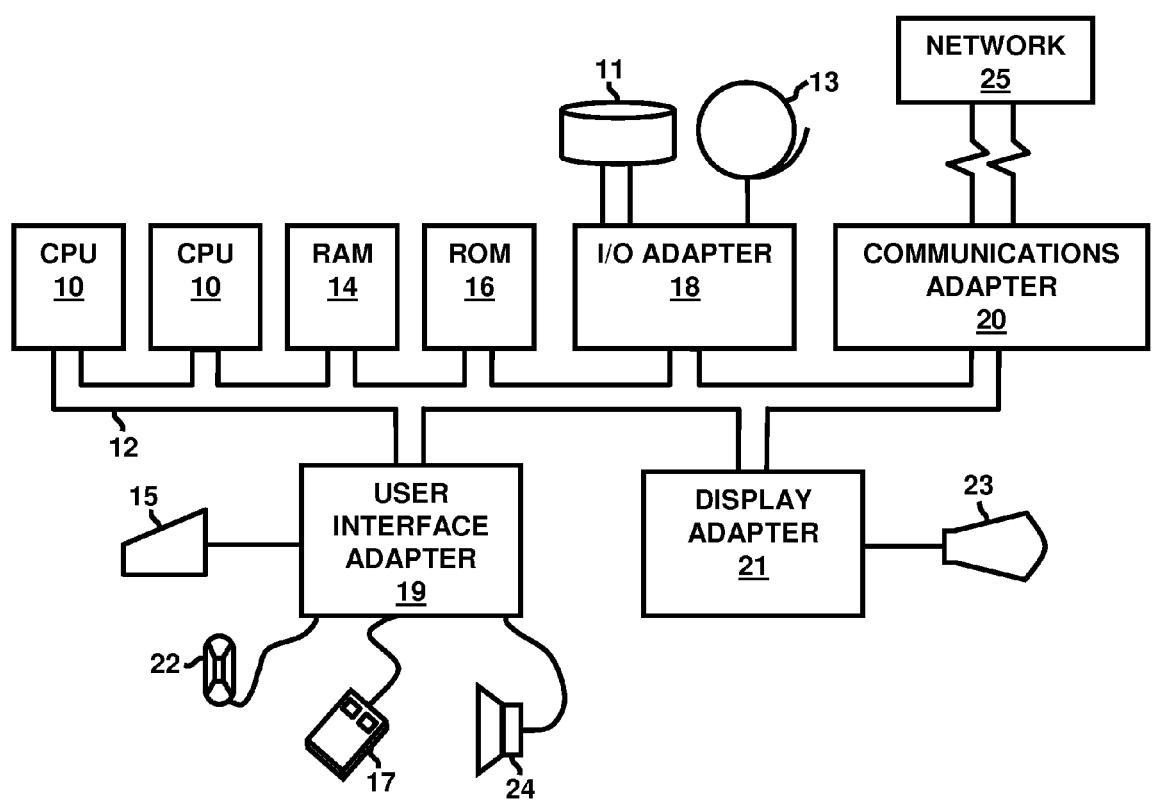
FIG. 6 illustrates a schematic diagram of a computer system used in accordance with the embodiments herein.

A representative hardware environment for practicing the embodiments herein is depicted in FIG. 6. This schematic drawing illustrates a hardware configuration of an information handling/computer system in accordance with the embodiments herein. The system comprises at least one processor or central processing unit (CPU) 10. The CPUs 10 are interconnected via system bus 12 to various devices such as a random access memory (RAM) 14, read-only memory (ROM) 16, and an input/output (I/O) adapter 18. The I/O adapter 18 can connect to peripheral devices, such as disk units 11 and tape drives 13, or other program storage devices that are readable by the system. The system can read the inventive instructions on the program storage devices and follow these instructions to execute the methodology of the embodiments herein. The system further includes a user interface adapter 19 that connects a keyboard 15, mouse 17, speaker 24, microphone 22, and/or other user interface devices such as a touch screen device (not shown) to the bus 12 to gather user input. Additionally, a communication adapter 20 connects the bus 12 to a data processing network 25, and a display adapter 21 connects the bus 12 to a display device 23 which may be embodied as an output device such as a monitor, printer, or transmitter, for example.

The techniques provided by the embodiments herein may be implemented on an integrated circuit (IC) chip (not shown) or using printable electronic technologies (not shown). The chip or printable electronic circuit design is created in a graphical computer programming language, and stored in a computer storage medium (such as a disk, tape, physical hard drive, or virtual hard drive such as in a storage access network). If the designer does not fabricate chips or printable electronic circuits or the photolithographic masks used to fabricate chips or printable electronic circuits, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII or CIF) for the fabrication of photolithographic masks, which typically include multiple copies of the chip design in question that are to be formed on a wafer or printed on a suitable substrate. The photolithographic masks are utilized to define areas of the wafer or printable electronic circuits (and/or the layers thereon) to be etched or otherwise processed or printed.

The resulting integrated circuit chips or printable electronic circuits can be distributed by the fabricator in raw wafer form (that is, as a single wafer that has multiple unpackaged chips), as a bare die, or in a packaged form or as individual printed circuits or in a sheet or roll of printed circuits. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip might then be integrated with other chips, discrete circuit elements, and/or other signal processing devices as part of either (a) an intermediate product, such as a mother or daughter-board, or (b) an end product. The end product can be any product that includes integrated circuit chip or chips and/or printed circuits, ranging from toys and other low-end applications to advanced computer products having a display, a keyboard or other input device, and a central processor.

The techniques provided by the embodiments herein may also be implemented on a printed circuit board (PCB) using discrete components. In this case, the electronic circuit components described herein, such as adder circuit, digital infinite impulse response (IIR) or finite impulse response (FIR) circuit, comparator circuit, metal-oxide-semiconductor field-effect transistor (MOSFET) pair, analog low-pass filter, can use discrete components and these discrete components are electronically connected on the printed circuit board to perform the functions described herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A database system comprising:
    at least one first computing device storing at least one database comprising medical-related data, wherein said at least one database comprises:
        a first module programmed with software that tangibly performs and adapts said at least one first computing device to store and retrieve data relating to pharmaceutical drugs, wherein said first module comprises:
            a first set of computer-executable commands relating to dosing of said pharmaceutical drugs;
            a second set of computer-executable commands relating to an efficacy and side effects of said pharmaceutical drugs;
            a third set of computer-executable commands relating to a cost of said pharmaceutical drugs;
            a fourth set of computer-executable commands relating to an accessibility and delivery of said pharmaceutical drugs; and
            a fifth set of computer-executable commands relating to mixing of a plurality of different pharmaceutical drugs and administering said plurality of different pharmaceutical drugs to a patient;

a second module programmed with software that tangibly performs and adapts said at least one first computing device to store and retrieve data relating to medical treatment protocols;

a third module programmed with software that tangibly performs and adapts said at least one first computing device to store and retrieve data relating to healthcare reimbursement data;

a fourth module programmed with software that tangibly performs and adapts said at least one first computing device to store and retrieve data relating to medical billing coding data; and a fifth module programmed with software that tangibly performs and adapts said at least one first computing device to store and retrieve data relating to medical education data, wherein said medical education data comprises:

a first set of computer-executable commands relating to medical literature retrieval of medical literature comprising textbooks, online databases, journal articles, graphics, interactive audio, and interactive video; and a second set of computer-executable commands relating to continuing medical education (CME) data, wherein said CME data comprises CME course listings and CME conference listings related to a medical subspecialty;

a communications channel operatively connected to said at least one database; and at least one second computing device comprising a cellular phone and operatively connected to said at least one database through said communications channel, wherein each of said at least one second computing device:

accesses all modules of said at least one database through said communications channel;

consolidates and stores both said medical-related data based on user instructions and a customized user profile onto said at least one second computing device, wherein said customized user profile is stored on said at least one first computing device and each said customized user profile stored on said at least one first computing device comprises a user profile of a medical practitioner, wherein said customized user profile comprises a medical subspecialty of said medical practitioner, and wherein the consolidated medical-related data comprises:

retrieved data relating to said pharmaceutical drugs;

retrieved data relating to said healthcare reimbursement data;

retrieved data relating to said medical treatment protocols;

retrieved data relating to said healthcare reimbursement data;

retrieved data relating to said medical billing coding data; and retrieved data relating to said medical education data; and broadcasts said consolidated medical-related data through said communications channel to said at least one first computing device, wherein said each of said at least one second computing device displays a webpage of an office of said medical practitioner and said webpage comprises a software module that processes patient appointments and interoffice communication.

2. The database system of claim 1, further comprising a host server operatively connected to said at least one database, wherein said host server transmits said medical-related data from said at least one database to said each of said at least one second computing device through said communications channel.

3. The database system of claim 1, wherein said each of said at least one second computing device comprises a handheld communications device.

4. The database system of claim 3, wherein said handheld communications device comprises any of a personal display assistant (PDA) and a cellular phone.

5. The database system of claim 1, wherein said customized user profile comprises software programmed to filter only medical subspecialty data from said medical-related data retrievable from said at least one database and transmit said medical subspecialty data.

6. The database system of claim 1, wherein said second module comprises: a first set of computer-executable commands relating to patient data; a second set of computer-executable commands relating to medical decision-making data in accordance with medical industry standards; and a third set of computer-executable commands comprising linking information to said first module relating to pharmaceutical drugs.

7. The database system of claim 6, wherein said patient data comprises any of age, illness type, and stage of illness data.

8. The database system of claim 1, wherein said third module a comprises: a first set of computer-executable commands relating to a cost of a particular medical protocol according to a particular type of medical insurance; a second set of computer-executable commands relating to a determination of whether a particular type of medical treatment is Federal Drug Administration (FDA) approved; and a third set of computer-executable commands relating to patient co-pay data.

9. The database system of claim 1, wherein said fourth module comprises: a first set of computer-executable commands relating to office visit scenarios for which a medical practitioner may bill a patient; and a second set of computer-executable commands that provide instructions to billing software for linking to a medical insurance supplier for providing healthcare reimbursement for said medical practitioner.

10. The database system of claim 1, wherein said consolidated data is broadcast in any of a text, graphics, audio, and video format.

11. The database system of claim 1, wherein said medical-related data comprises oncology-related data.

12. The database system of claim 1, further comprising a separate database for each one of said modules.

13. The database system of claim 1, wherein said each of said at least one second computing device comprises an interface that receives said user instructions.

14. The database system of claim 13, wherein said interface comprises any of a microphone, stylus, mouse, and keypad.

15. The database system of claim 1, wherein said user instructions comprise any of a user query and said customized user-profile that instructs said at least one database to transmit particular medical-related data specific to said user instructions.

16. A method of managing medical-related data tangibly performed and executed by a computing device, said method comprising:

storing, by said computing device, a first type of medical-related data relating to pharmaceutical drugs, wherein said first type of medical-related data comprises:
  a first set of computer-executable commands relating to dosing of said pharmaceutical drugs;
  a second set of computer-executable commands relating to an efficacy and side effects of said pharmaceutical drugs;
  a third set of computer-executable commands relating to a cost of said pharmaceutical drugs;
  a fourth set of computer-executable commands relating to an accessibility and delivery of said pharmaceutical drugs; and
  a fifth set of computer-executable commands relating to mixing of a plurality of different pharmaceutical drugs and administering said plurality of different pharmaceutical drugs to a patient;
storing, by said computing device, a second type of medical-related data relating to medical treatment protocols;
storing, by said computing device, a third type of medical-related data relating to healthcare reimbursement data;
storing, by said computing device, a fourth type of medical-related data relating to medical billing coding data;
storing, by said computing device, a fifth type of medical-related data relating to medical education data wherein said medical education data comprises:
  a first set of computer-executable commands relating to medical literature retrieval of medical literature comprising textbooks, online databases, journal articles, graphics, interactive audio, and interactive video; and
  a second set of computer-executable commands relating to continuing medical education (CME) data, wherein said CME data comprises CME course listings and CME conference listings related to a medical subspecialty;
providing user instructions for retrieving the first, second, third, fourth, and fifth types of medical-related data through a communications channel;
accessing said first, second, third, fourth, and fifth types of medical-related data stored on said computing device;
consolidating, and storing, said first, second, third, fourth, and fifth types of medical-related data based on said user instructions and a customized user profile on said computing device; and
broadcasting said consolidated medical-related data through said communications channel to a central computing device,
wherein said customized user profile is stored on said computing device and comprises a user profile of a medical practitioner,
wherein said user profile comprises a medical subspecialty of said medical practitioner,
wherein said consolidated medical-related data comprises:
  retrieved data relating to said pharmaceutical drugs;
  retrieved data relating to said healthcare reimbursement data;
  retrieved data relating to said medical treatment protocols;
  retrieved data relating to said healthcare reimbursement data;
  retrieved data relating to said medical billing coding data; and
  retrieved data relating to said medical education data, wherein said medical education data comprises journal articles related to said medical subspecialty,
wherein said computing device comprises a cellular phone and said computing device displays a webpage of an office of said medical practitioner and said webpage comprises a software module that processes patient appointments and interoffice communication.

17. A non-transitory program storage device readable by a computer comprising a program of instructions executable by said computer to perform a computer-automated method of managing medical-related data, said method comprising:
storing a first type of medical-related data relating to pharmaceutical drugs, wherein said first type of medical-related data comprises:
  a first set of computer-executable commands relating to dosing of said pharmaceutical drugs;
  a second set of computer-executable commands relating to an efficacy and side effects of said pharmaceutical drugs;
  a third set of computer-executable commands relating to a cost of said pharmaceutical drugs;
  a fourth set of computer-executable commands relating to an accessibility and delivery of said pharmaceutical drugs; and
  a fifth set of computer-executable commands relating to mixing of a plurality of different pharmaceutical drugs and administering said plurality of different pharmaceutical drugs to a patient;
storing a second type of medical-related data relating to medical treatment protocols;
storing a third type of medical-related data relating to healthcare reimbursement data;
storing a fourth type of medical-related data relating to medical billing coding data;
storing a fifth type of medical-related data relating to medical education data, wherein said medical education data comprises:
  a first set of computer-executable commands relating to medical literature retrieval of medical literature comprising textbooks, online databases, journal articles, graphics, interactive audio, and interactive video; and
  a second set of computer-executable commands relating to continuing medical education (CME) data, wherein said CME data comprises CME course listings and CME conference listings related to a medical subspecialty;
providing user instructions for retrieving the first, second, third, fourth, and fifth types of medical-related data through a communications channel;
accessing said first, second, third, fourth, and fifth types of medical-related data stored on said computer;
consolidating, and storing, said first, second, third, fourth, and fifth types of medical-related data based on said user instructions on said computer; and
broadcasting said first, second, third, fourth, and fifth types of consolidated medical-related data through said communications channel to a central computer,
wherein said consolidated medical-related data comprises:
  retrieved data relating to said pharmaceutical drugs;
  retrieved data relating to said healthcare reimbursement data;
  retrieved data relating to said medical treatment protocols;
  retrieved data relating to said healthcare reimbursement data; and
  retrieved data relating to said medical billing coding data,
wherein said computer comprises a cellular phone and said computer displays a webpage of an office of said medical practitioner and said webpage comprises a software module that processes patient appointments and interoffice communication.

* * * * *